United States Patent [19]
Nokihara

[11] Patent Number: 5,362,447
[45] Date of Patent: Nov. 8, 1994

[54] AUTOMATED PEPTIDE SYNTHESIZER
[75] Inventor: Kiyoshi Nokihara, Kyoto, Japan
[73] Assignee: Shimadzu Corporation, Kyoto, Japan
[21] Appl. No.: 131,618
[22] Filed: Oct. 5, 1993
[30] Foreign Application Priority Data
 Oct. 13, 1992 [JP] Japan .................. 4-301775
[51] Int. Cl.$^5$ ................. B01J 8/02; C07C 103/52
[52] U.S. Cl. ....................... 422/131; 422/62;
 422/68.1; 422/116; 422/125; 422/134; 436/89;
 935/87; 935/88
[58] Field of Search ............. 422/62, 68.1, 70, 81,
 422/125, 116, 111, 131, 135, 134; 436/89, 173;
 935/87, 88

[56] References Cited
U.S. PATENT DOCUMENTS
 4,362,699 12/1982 Verlander et al. ............ 422/131
 4,748,002 5/1988 Neimark et al. .............. 422/116

FOREIGN PATENT DOCUMENTS
 0156588 10/1985 European Pat. Off. ....... B01J 19/00
 4005518 8/1991 Germany ................. C07K 1/04
 WO9312427 6/1993 WIPO .................... G01N 33/68

OTHER PUBLICATIONS
Merrifield, Solid Phase Synthesis, Science 232, pp. 341-347, Apr. 18, 1986.

*Primary Examiner*—David A. Redding
*Attorney, Agent, or Firm*—Birch, Stewart, Kolasch & Birch

[57] ABSTRACT

The present invention is directed to an automated peptide synthesizer equipped with recovery lines including an acyl component recovery line for recovering unreacted acyl components to allow the reuse of the acyl components, and a solvent recovery line for recovering and distilling a reaction solvent and passing it through a purification column to allow the reuse of the reaction solvent. Both recovery lines are installed on the flow pathway from one or more reaction chambers or columns to a waste liquid reservoir of the automated peptide synthesizer. By recovering expensive acyl components and solvents, running cost in peptide synthesis can be reduced to mitigate economic burden, and the amount of waste leading to environmental destruction can be reduced.

4 Claims, 1 Drawing Sheet

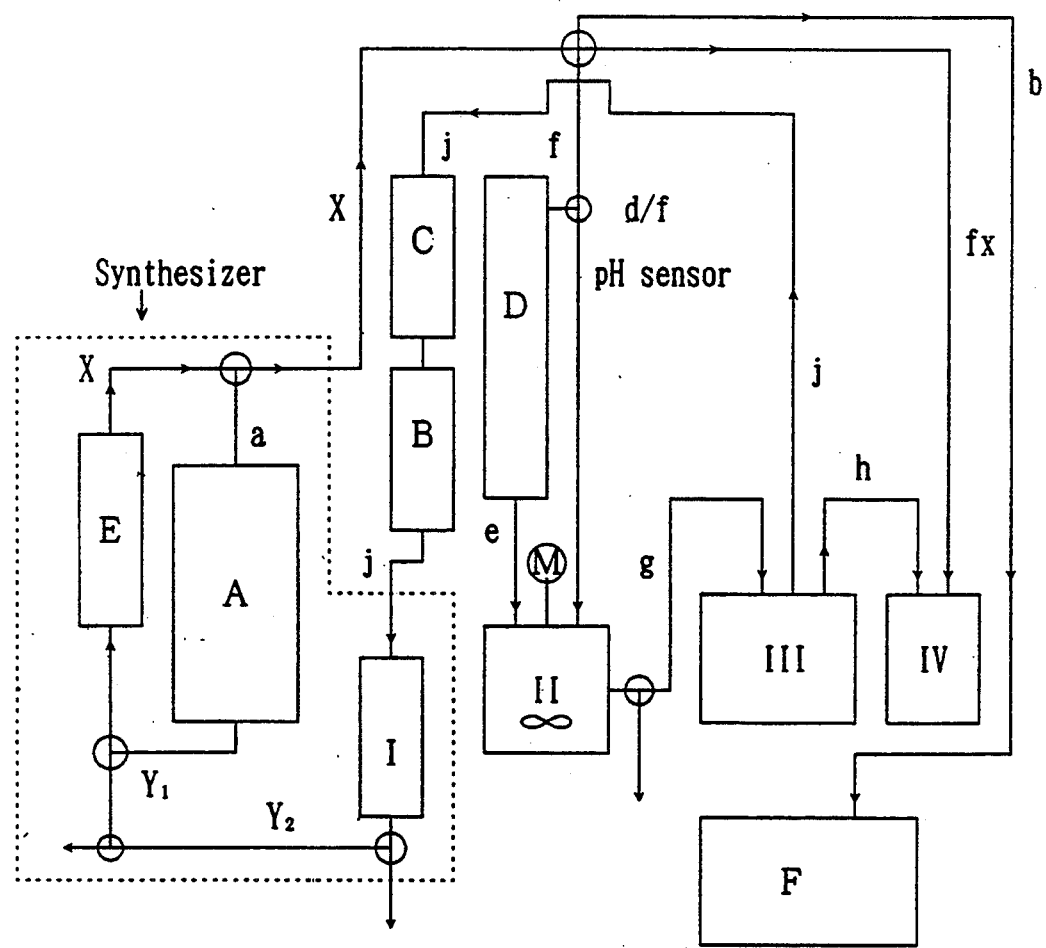
F I G. 1

AUTOMATED PEPTIDE SYNTHESIZER

BACKGROUND OF THE INVENTION

1. Field of the Invention

The present invention relates an automated peptide synthesizer, and more particularly to an automated peptide synthesizer having flow pathways for recovering unreacted acyl components and reaction solvents.

2. Discussion of the Related Art

Solid-phase peptide synthesis is a technique for synthesizing the desired peptide by repeating a step of deprotection and acyl component introduction in the process of sequential couplings of amino acids on a solid-phase support. This technique is basically one of chemical synthesis, in which a great excess of acyl components is sequentially reacted to permit the synthesis to proceed without confirmation of intermediates. The number of repeats of this synthesis step increases as the number of amino acids of the peptide chain increases, and because the remaining components such as acyl components remaining in the reaction product are potential contaminants for the following repeated synthesis step, they should be washed out with an organic solvent. This washing step requires an enormous amount of organic solvent For example, in the BOC method using methylene chloride, more than about 10 liters of the waste solvent is discharged when 1 g of a peptide consisting of 5 amino acid residues is synthesized.

Acyl components such as protected amino acids and protected peptide fragments are very expensive. Even when a 10-fold amount of the acyl components is used, 90% thereof is wasted since the amount of the acyl components actually involved in the reaction is theoretically equivalent. However, usually a 4-fold amount or more of the acyl components must be used in order to complete the reaction on a solid-phase support. This means that the cost of acyl components cannot be overlooked when a large-scale synthesis is employed, as contrasted with minor economic burden in experimentation or in a small-scale synthesis.

Also, solvents used for peptide synthesis such as dimethylformamide (DMF), methylene chloride, N-methylpyrrolidone and dimethylacetamide are not harmless substances and can cause environmental pollution when wasted, requiring an enormous amount of cost for their recovery and treatment. In particular, DMF, a frequently used solvent, is known to sometimes contain amine compounds as impurities and causes side reactions in the process of synthesis. Therefore, removal of trace amounts of amines and water from the reaction solvent allows synthesis at a high efficiency.

SUMMARY OF THE INVENTION

The present inventor has conducted investigations to develop an automated peptide synthesizer meeting the requirements of (1) running cost reduction in a large-scale peptide synthesis, and (2) prevention of environmental pollution (prevention of environmental destruction).

As a result, the present inventor has found that the recovered reaction reagents can be purified, to such an extent that its reuse is possible, by providing a line for recovering and purifying reaction reagents such as a solvent and a line for recovering acyl components on the flow pathway from the reaction chamber to a waste liquid reservoir, in which these lines are controlled by valve operation according to each reaction process. The present inventor has further conducted investigations based on this finding, and thus has developed the present invention.

Accordingly, the present invention relates to an automated peptide synthesizer equipped with recovery lines comprising a line for recovering the unreacted acyl components, and a line for recovering and distilling a reaction solvent and passing it through a purification column to allow the reuse of the reaction solvent, both recovery lines being installed on the flow pathway from a reaction chamber to a waste liquid reservoir of the automated peptide synthesizer.

BRIEF DESCRIPTION OF THE DRAWING

The present invention will become more fully understood from the detailed description given hereinbelow and the accompanying drawings which are given by way of illustration only, and thus, are not limitative of the present invention, and wherein:

FIG. 1 is a schematic view showing a process flow sheet of the acyl component recovery line and the solvent recovery line in the automated peptide synthesizer of the present invention.

The reference numerals in FIG. 1 denote the following elements:

Element I is a solvent chamber, element II a recovery chamber, element III a continuous distilling device, element IV a waste liquid reservoir, element A an acyl component preparation chamber, element B a column, element C a column, element D a reagent supplying unit, element E a reaction chamber (a reaction column), and element F a fraction collector.

DETAILED DESCRIPTION OF THE PREFERRED EMBODIMENT

In the present invention, by providing an acyl component recovery line and a solvent recovery line on the flow pathway from the reaction chamber to the waste liquid reservoir of an automated peptide synthesizer, the unreacted acyl components can be recovered from a waste liquid discharged from the reaction chamber to allow the reuse of amino acid derivatives which are expensive acyl components, and also reaction solvents can be recovered and purified to allow their reuse. It is, therefore, possible to solve the problem of production cost reduction, including yield and purity, in a large-scale peptide synthesis, and also to significantly reduce the amount of the waste liquid, which causes environmental destruction.

The present invention is hereinafter described by referring to FIG. 1.

Pathways "$Y_1$", "$Y_2$" and "X-fx" are, respectively, acyl component supplying pathway, solvent supplying pathway and waste liquid pathways in a conventional peptide synthesizer. Switching of pathways "X" and "a" and that of pathways "f" and "fx" are achieved under valve operating direction by a computer (not illustrated) which controls peptide synthesis. In the peptide synthesizer, one or more reaction chambers are used. Instead of the reaction chamber, one or more reaction columns may be used.

(1) Recovery of acyl components

An acyl component preparation chamber A is preferably a detachable cartridge. In an ordinary peptide synthesis, the acyl components which are preactivated such as an active ester are used. The acyl components used in the peptide synthesis is activated by a reagent, and is introduced to a reaction chamber (column) E in the form of, for instance, an active ester, whose side chain functional group and Nα amino group are protected. After completion of the reaction, the acyl components are recovered by a means for recovering such as by using fraction collector F via a pathway "b". The recovered acyl components contain the unreacted acyl components, added amine, hydroxybenzotriazole (HOBt) used for activation and other substances.

The acyl components recovered in the fraction collector F is manually or semi-automatically regenerated, thereby making it possible to reuse it as a protected amino acid derivative. When the acyl components used are not an amino acid derivative but a protected peptide fragment, recovery is more important for cost performance.

General procedures for the recovery and regeneration of the acyl components are as follows:

After the coupling reaction, the unreacted acyl component in DMF is recovered to a fraction collector F via a pathway "X" and a pathway "b". The resulted solution (acyl component) is concentrated. The resultant gum or oil is triturated with a saturated NaHCO$_3$ solution, and the solid and/or precipitate is washed with water. By this procedure, an active ester is hydrolyzed.

When the resulting solid is soluble in ethyl acetate, the acyl components are extracted by washing with 1M citric acid and rapidly with a saturated NaHCO$_3$ solution, adjusted to a pH of 4 to 5 with 0.1 N HCl, followed by washing with a saturated NaCl solution. Then, the organic layer is dried over MgSO$_4$ or Na$_2$SO$_4$. The obtained mixture is concentrated and precipitated from petroleum ether and/or solidified.

Are thus recovered protected amino acids or protected fragments used for the acyl component are recrystallized or reprecipitated from appropriate solvents.

When the activated acyl components are insoluble in ethyl acetate, an aqueous solution of sodium hydrogen carbonate is added to precipitate the amino acid whose NH$_2$ group at the α position and functional groups of side chain are protected or to precipitate a protected peptide fragment on the basis of the principle that an aqueous solution of sodium hydrogen carbonate hydrolyzes the active ester. The precipitate is then collected and thoroughly washed with water.

The purity of the recrystallized or reprecipitated product is determined by thin-layer chromatography, high performance liquid chromatography, mass spectrometry, DL analysis, optical rotation analysis, etc.

(2) Recovery of solvent from waste liquid

The solvent used for washing the reaction chamber (column) E is sent to a recovery chamber II via a pathway "X." On this route, a pathway "f" for solvent recovery is provided. It is preferable to provide a pathway "f" with a means for sensing a pH change before distillation of the recovered solvent and neutralizing the acid and base therein. For example, when a pH sensor on d/f of the pathway "f" senses a pH change in the waste liquid, a neutralizing reagent is sent to the recovery chamber II via a pathway "e" from a reagent supplying unit D to neutralize the acid or base in the solvent being recovered. From the reagent supplying unit D, is supplied a neutralizing reagent such as dilute hydrochloric acid in, for example, DMF.

The recovery chamber II has a stirring motor M therein, which offers as uniform stirring as possible. The recovered waste liquid is further introduced to a continuous distiller III via a pathway "g". The pathway "g" has a filter having a pore size, for instance, of 2 μm, and the waste liquid which passes the filter is transferred to the continuous distiller III, while the solids are removed from this purification pathway.

The continuous distiller III performs a precision distillation. Waste liquids containing large amounts of high-boiling point substances, residues (e.g., the rest amount of amino acid derivatives) and components whose recovery does not warrant the cost of their reuse in the synthesis process, such as reagents for deprotection, are selectively introduced to the waste liquid reservoir IV via a pathway "h" or "fx". The continuous distiller III may be used singly or in a combination of two or more.

The distilled solvent for reuse is introduced to a solvent chamber I of the peptide synthesizer through some columns (for instance, C and B) via a pathway "j" and supplied to the reaction chamber. These columns may be, for instance, packed with molecular sieves or activated charcoals to remove water, small amount of amines, etc. from the distilled solvent, which may contain trace amounts of water, degradation products during distillation, etc.

The acyl component recovery line and the solvent recovery line in the present invention are installed in a continuous flow or batch-wise peptide synthesizer of large capacity. The recovery is performed by a valve switch in accordance with the progress of each procedure.

By recovering expensive acyl components and solvents, running cost in peptide synthesis for large amounts exceeding 5 g of a peptide can be reduced to mitigate economic burden, and the amount of waste leading to environmental destruction can be reduced.

Moreover, the present invention reduces the cost required for the purchase of starting materials, the treatment of waste liquid, etc. by significantly reducing the amount of the starting material actually consumed and the waste liquid (organic solvent) which can cause environmental destruction.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An automated peptide synthesizer comprising an acyl component preparation chamber, one or more reactions chambers or reaction columns, computer means for controlling peptide synthesis, a solvent chamber and recovery lines which lines comprise:

an acyl component recovery line for recovering unreacted acyl components to allow the reuse of the acyl components, and a solvent recovery line including a solvent recovery chamber, solvent distilling device, and solvent purification column for recovering, distilling, and purifying a reaction solvent to allow the reuse of the reaction solvent, both recovery lines being installed on the flow pathway from one or more reaction chambers or columns to a waste liquid reservoir of the automated peptide synthesizer.

2. The automated peptide synthesizer according to claim 1, wherein said unreacted acyl components are recovered in a fraction collector.

3. An automated peptide synthesizer comprising an acyl component preparation chamber, one or more reaction chambers or reaction columns, computer means for controlling peptide synthesis, a solvent chamber and recovery lines which lines comprise:

an acyl component recovery line for recovering unreacted acyl components to allow the reuse of the acyl components, and a solvent recovery line for recovering and distilling a reaction solvent and for passing it through a purification column to allow the reuse of the reaction solvent, wherein said solvent recovery line comprises a recovery chamber, a continuous distilling device and a column packed with molecular sieves or activated charcoals for a further purification of the distilled solvent, both recovery lines being installed on the flow pathway from one or more reaction chambers or columns to a waste liquid reservoir of the automated peptide synthesizer.

4. The automated peptide synthesizer according to claim 3, wherein said solvent recovery line further comprises a means for detecting a change in pH before distilling the recovered solvent and a means for neutralizing acids or bases in the recovered solvent.

* * * * *